United States Patent
Shin et al.

(10) Patent No.: US 10,617,608 B2
(45) Date of Patent: Apr. 14, 2020

(54) COMPOSITION FOR HYDROGEL SHEET, HYDROGEL SHEET MANUFACTURED THEREFROM, AND METHOD FOR MANUFACTURING SAME

(71) Applicant: LOTTE FINE CHEMICAL CO., LTD., Ulsan (KR)

(72) Inventors: Ju Hee Shin, Incheon (KR); Ji Seon Jeong, Incheon (KR); Sung Hwan Bang, Incheon (KR); Ju Young Jung, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

(21) Appl. No.: 15/762,989

(22) PCT Filed: Sep. 23, 2016

(86) PCT No.: PCT/KR2016/010709
§ 371 (c)(1),
(2) Date: Mar. 23, 2018

(87) PCT Pub. No.: WO2017/052301
PCT Pub. Date: Mar. 30, 2017

(65) Prior Publication Data
US 2018/0214354 A1 Aug. 2, 2018

(30) Foreign Application Priority Data

Sep. 25, 2015 (KR) .................... 10-2015-0136129
Sep. 22, 2016 (KR) .................... 10-2016-0121762

(51) Int. Cl.
*A61Q 19/00* (2006.01)
*C08L 1/00* (2006.01)
(Continued)

(52) U.S. Cl.
CPC ............ *A61K 8/0212* (2013.01); *A61K 8/042* (2013.01); *A61K 8/20* (2013.01); *A61K 8/73* (2013.01);
(Continued)

(58) Field of Classification Search
CPC ........ A61K 8/0212; A61K 8/042; A61K 8/20; A61K 8/73; A61K 8/731
See application file for complete search history.

(56) References Cited

U.S. PATENT DOCUMENTS 7,816,341 B2 * 10/2010 Sewall .................... A61K 8/11
424/451
2010/0112058 A1 5/2010 Lim et al.

FOREIGN PATENT DOCUMENTS

EP        0714656 A1 * 6/1996 ........... A61K 9/4816
KR     20010014728 A    2/2001
(Continued)

OTHER PUBLICATIONS

Reliability Direct ([online] retrieved on Jun. 27, 2019 from: http://www.reliabilitydirectstore.com/v/vspfiles/RDIStorePDF/Viscosity%20Conversion%20Chart. (Year: 2019).*
(Continued)

*Primary Examiner* — Ernst V Arnold
(74) *Attorney, Agent, or Firm* — Osha Liang LLP

(57) ABSTRACT

The present invention relates to a composition for a hydrogel sheet including a cellulose ether, a gelling agent, and a gelling promoter, a hydrogel sheet prepared therefrom, and a method of preparing the hydrogel sheet. According to the present invention, the composition for a hydrogel sheet can be used to prepare a hydrogel sheet capable of maintaining the shape thereof without a support by limiting a type of the gelling agent and/or a viscosity of the cellulose ether included in the composition.

3 Claims, 4 Drawing Sheets

(51) Int. Cl.
*A61K 8/02* (2006.01)
*A61K 8/73* (2006.01)
*A61K 8/04* (2006.01)
*A61K 8/20* (2006.01)
*A61L 15/22* (2006.01)
*A61L 15/28* (2006.01)
*A61L 15/42* (2006.01)

(52) U.S. Cl.
CPC ............ *A61K 8/731* (2013.01); *A61L 15/225* (2013.01); *A61L 15/28* (2013.01); *A61L 15/425* (2013.01); *A61Q 19/00* (2013.01)

(56) References Cited

FOREIGN PATENT DOCUMENTS

| | | |
|---|---|---|
| KR | 101206263 B1 | 11/2012 |
| KR | 2013-0036543 A | 4/2013 |
| KR | 2013-0046842 A | 5/2013 |
| KR | 20140116325 A | 10/2014 |
| KR | 20150082792 A | 7/2015 |
| WO | WO-2013164121 A1 * | 11/2013 ........... A61K 9/4816 |

OTHER PUBLICATIONS

International Search Report issued in PCT/KR2016/010709 dated Jan. 24, 2017 (2 pages).
Written Opinion issued in PCT/KR2016/010709 dated Jan. 24, 2017 (7 pages).

* cited by examiner

[FIG. 1]
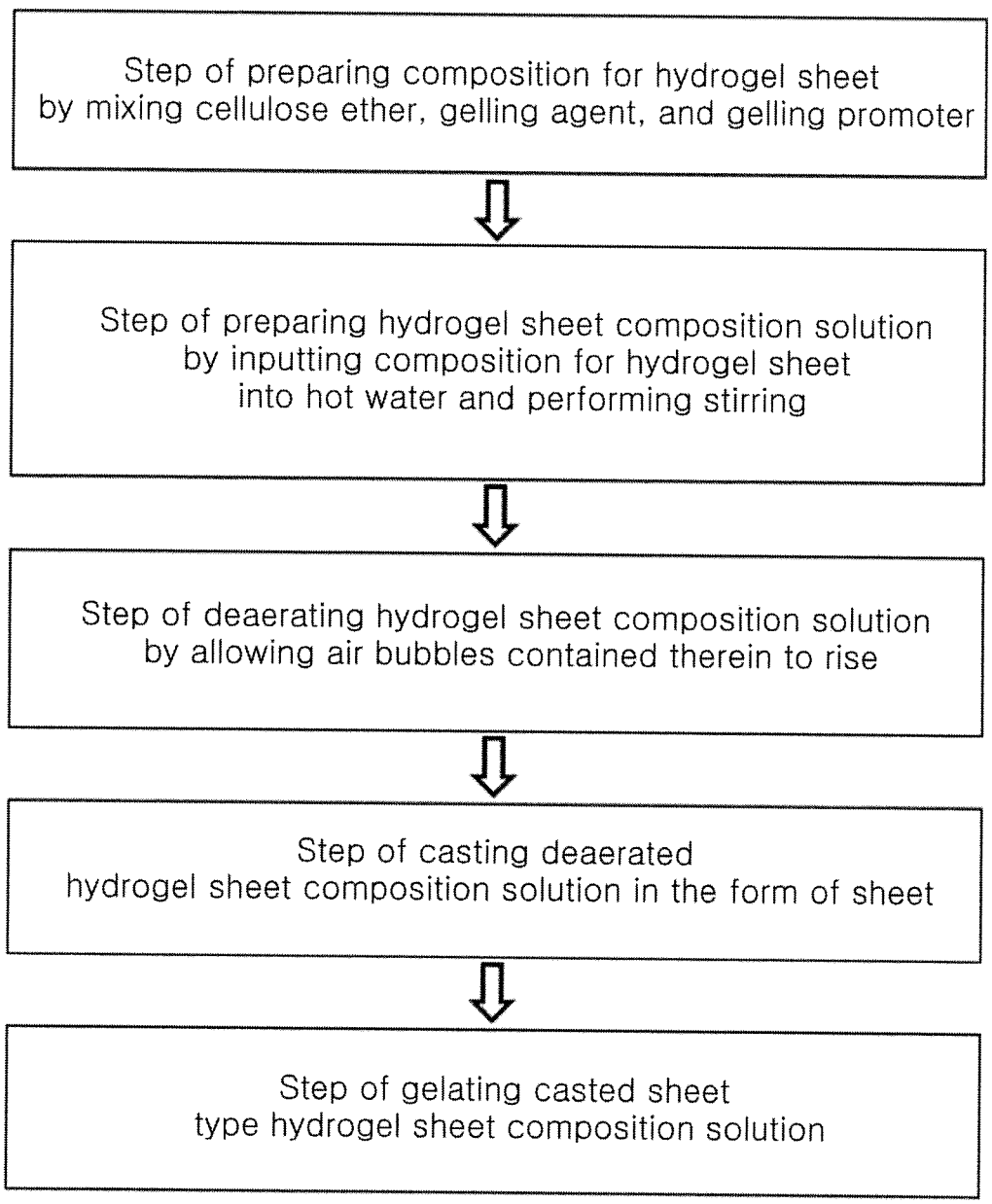

[FIG. 2]
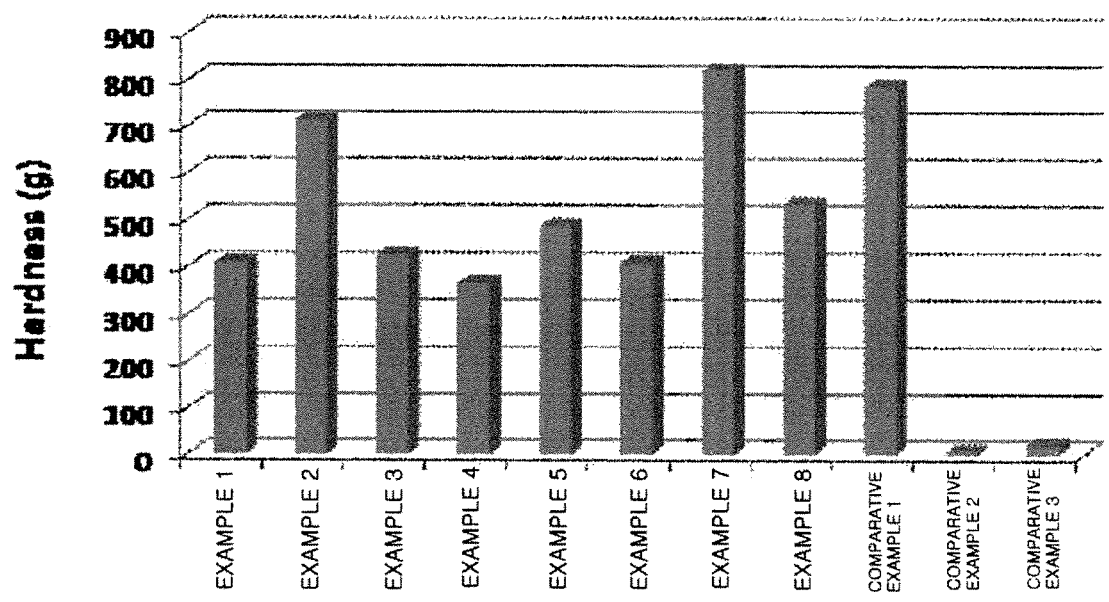
[FIG. 3]
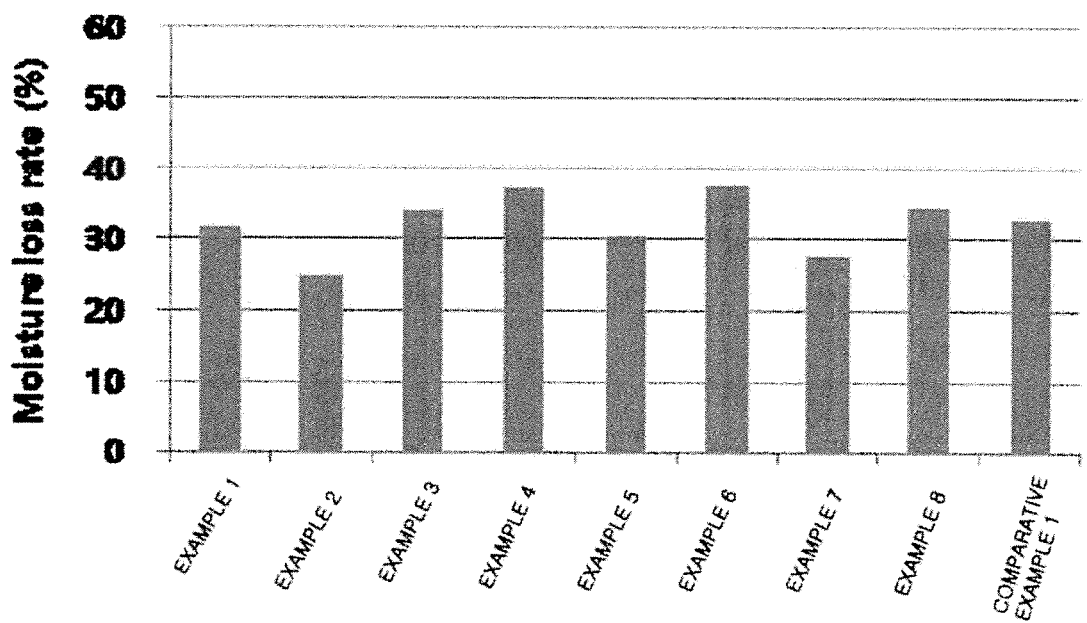

[FIG. 4]
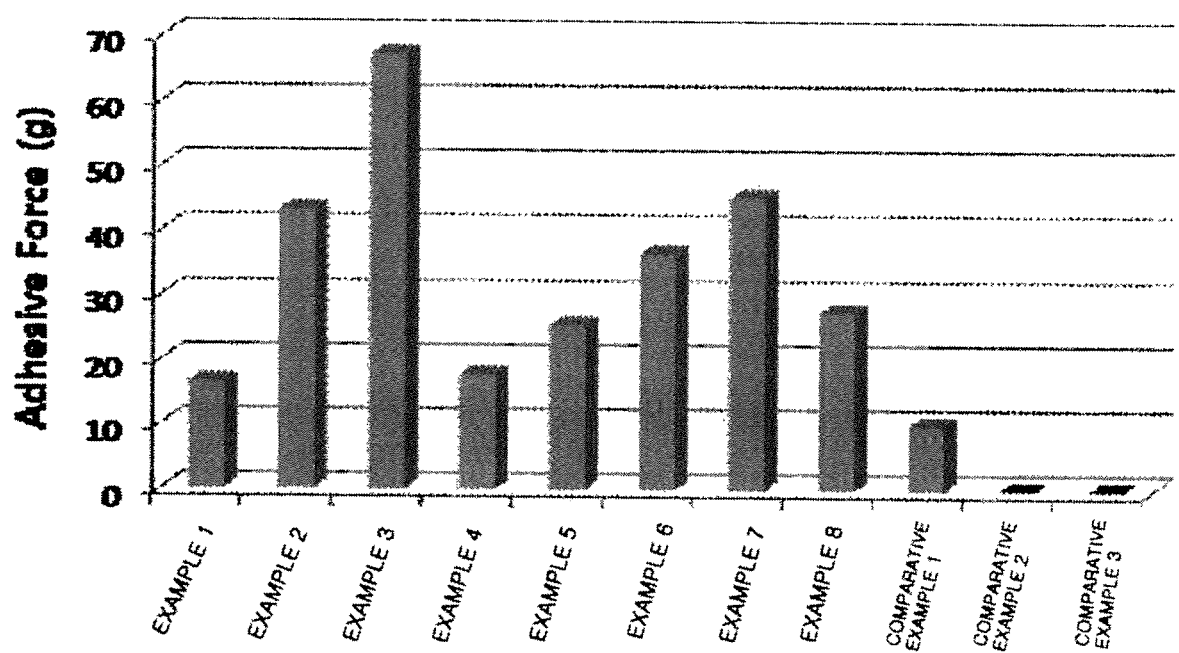
[FIG. 5]

[FIG. 6]
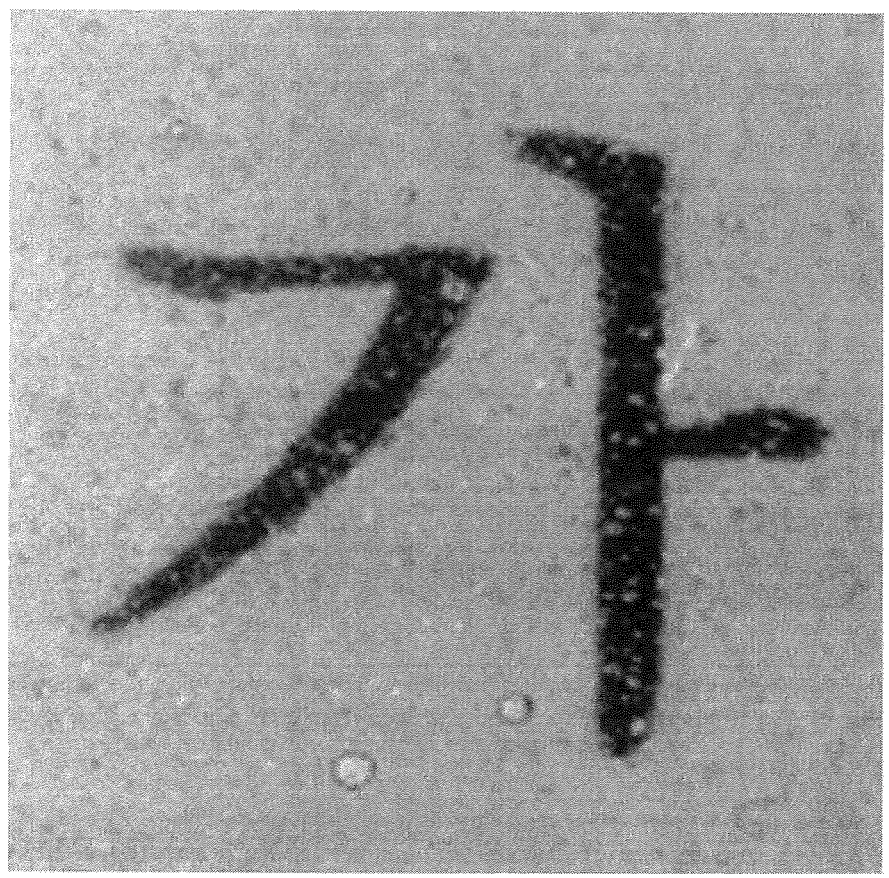

COMPOSITION FOR HYDROGEL SHEET, HYDROGEL SHEET MANUFACTURED THEREFROM, AND METHOD FOR MANUFACTURING SAME

TECHNICAL FIELD

The present invention relates to a composition for a hydrogel sheet, a hydrogel sheet prepared therefrom, and a method of preparing the hydrogel sheet, and more particularly, to a composition for a hydrogel sheet which includes a cellulose ether, a gelling agent, and a gelling promoter, and thus may be used to prepare a hydrogel sheet capable of maintaining the shape thereof without a support, a hydrogel sheet prepared therefrom, and a method of preparing the hydrogel sheet.

BACKGROUND ART

A hydrogel is a network of hydrophilic polymer chains in which water is the dispersion medium. The hydrogel can contain a large amount of water in the structure thereof because it is not dissolved, but swelled in water, and thus it possesses a degree of flexibility very similar to natural tissue.

The hydrogel has been used in the medical and pharmaceutical field, such as the fields of tissue engineering, cell culture, sustained-release drug delivery systems, biosensors, soft lenses, medical electrodes, and the like, due to its unique hydrophilicity and flexibility, and has also been applied in the cosmetic field to prepare a mask pack for delivering various advantageous effects including moisturizing, nourishing, wrinkle improvement, whitening, and the like to skin.

In the case of an application in a mask pack, research on and the development of a method of preparing a sheet type hydrogel are being actively conducted. Conventionally, when a hydrogel is prepared in the form of a sheet, the shape thereof cannot be maintained only by a hydrogel, and it has poor mechanical properties such as low strength or low hardness. Therefore, it is common to use a hydrogel in addition to a support such as a synthetic resin, a non-woven fabric, a mesh, or a net. However, a mask pack using a support such as a non-woven fabric or the like as a base is easily dried and has poor adhesion to skin, and a hydrogel is often detached from the support. In addition, since a support such as a non-woven fabric and the like is prepared through a chemical process, when a mask pack including such a support as a base is applied to skin, skin trouble may occur, and thus many safety evaluations and reviews are required.

As a method for solving these problems, Patent Document 1 (Korean Laid-Open Patent Publication No. 10-2013-0036543) discloses a hydrogel composition for a base of a mask capable of maintaining the shape thereof without a support and a method of preparing a hydrogel using the same. Specifically, the hydrogel composition includes 0.1 to 10 wt % of a crosslinking agent, 0.2 to 6 wt % of a gelling polymer, 0.5 to 20 wt % of a polyhydric alcohol, and 70 to 90 wt % of purified water, and the method of preparing a hydrogel includes (i) preparing an aqueous solution by adding a crosslinking agent to purified water at room temperature and then stirring the mixture at 40 to 85° C.; (ii) preparing a hydrogel composition by dissolving a gelling polymer in a polyhydric alcohol at room temperature, then adding a resulting substance to the aqueous solution, and stirring the mixture at 40 to 80° C.; (iii) compression coating the hydrogel composition so as to have a thickness of 0.5 to 2 mm; (iv) preparing a hydrogel by cooling the hydrogel composition layer prepared through compression coating at room temperature; and (v) thermally treating the hydrogel thus cooled at 40 to 85° C. for 12 to 36 hours.

According to the step (ii), a liquid hydrogel composition is prepared through a heating and stirring process. In this process, a large amount of air bubbles may be generated in the liquid hydrogel composition, and if the air bubbles thus generated are not removed, a resulting hydrogel sheet may be adversely affected. Specifically, when the liquid hydrogel composition is solidified into a hydrogel sheet while still containing a large number of air bubbles, an opaque and aesthetically unappealing hydrogel sheet is prepared. Not only that, since air bubbles trapped inside the solidified hydrogel prevent the hydrogel from having a three-dimensional network structure, a gel sheet with poor properties such as low gel strength is prepared.

PRIOR-ART DOCUMENT

Patent Document

1. KR 1020130036543 A

DISCLOSURE

Technical Problem

It is an aspect of the present invention to provide a composition for a hydrogel sheet which includes a cellulose ether, a gelling agent, and a gelling promoter, and thus may be used to prepare a hydrogel sheet capable of maintaining the shape thereof without a support.

It is another aspect of the present invention to provide a composition for a hydrogel sheet which may be used to prepare a hydrogel sheet that strongly adheres to the skin and has excellent stability and excellent moisturizing ability.

It is still another aspect of the present invention to provide a composition for a hydrogel sheet from which air bubbles generated during a process of preparing a hydrogel sheet composition solution may be easily removed to prepare a hydrogel sheet having excellent strength and a transparent appearance. The term "hydrogel sheet composition solution" used herein refers to a liquid state in which a solid content is dispersed, dissolved, or partially dissolved in hot water, and encompasses a dispersion, a dissolution, or a partial dissolution.

It is yet another aspect of the present invention to provide a hydrogel sheet prepared from the above-described composition and a method of preparing the hydrogel sheet.

Technical Solution

In order to accomplish the above objective, there are provided compositions for a hydrogel sheet according to two embodiments of the present invention.

A composition for a hydrogel sheet according to a first embodiment of the present invention includes a cellulose ether, a gelling agent including carrageenan, and a gelling promoter.

According to the first embodiment of the present invention, the gelling agent may further include one or more selected from the group consisting of locust bean gum, mannose, and water chestnut flour.

A composition for a hydrogel sheet according to a second embodiment of the present invention includes a cellulose ether, a gelling agent, and a gelling promoter, wherein a viscosity of an aqueous 2 wt % cellulose ether solution measured under a condition of 20° C. using an Ubbelohde viscometer is 3 cps to 300 cps.

According to the second embodiment of the present invention, the gelling agent may include one or more selected from the group consisting of carrageenan, locust bean gum, mannose, and water chestnut flour.

According to the second embodiment of the present invention, a viscosity of an aqueous 5 wt % hydrogel sheet composition solution measured under conditions of 60° C. and 15 to 60 rpm using a Brookfield viscometer may be 500 cps to 5,000 cps.

According to the first or second embodiment of the present invention, the cellulose ether may include one or more selected from the group consisting of methyl cellulose, hydroxyethyl methyl cellulose, hydroxypropyl methyl cellulose, hydroxyethyl cellulose, hydroxypropyl cellulose, and carboxymethyl cellulose.

According to the first or second embodiment of the present invention, the gelling promoter may be a Group 1 or 2 metal salt.

According to the first or second embodiment of the present invention, the gelling promoter may include one or more metal salts selected from the group consisting of magnesium chloride, potassium chloride, calcium chloride, and sodium chloride.

According to the first or second embodiment of the present invention, a molar ratio of a repeat unit of the gelling agent and a molar ratio of the gelling promoter, per a glucose unit of the cellulose ether, may be 0.01 to 12.00 and 0.01 to 2.00, respectively.

In addition, there is provided a hydrogel sheet prepared from the composition for a hydrogel sheet according to the first or second embodiment of the present invention.

The hydrogel sheet may have a porosity of 0.01% to 5%.

The hydrogel sheet may be used for a cosmetic mask pack or a wound dressing.

In addition, there is provided a method of preparing a hydrogel sheet from the above-described composition for a hydrogel sheet, which includes preparing a composition for a hydrogel sheet by mixing a cellulose ether, a gelling agent, and a gelling promoter; preparing a hydrogel sheet composition solution by inputting the composition for a hydrogel sheet into hot water and stirring the mixture; deaerating the hydrogel sheet composition solution by allowing air bubbles contained therein to rise; casting the deaerated hydrogel sheet composition solution in the form of a sheet; and gelating the casted sheet type hydrogel sheet composition solution.

A temperature of the hot water may be 70° C. to 100° C.

The deaeration may be performed by maintaining the hydrogel sheet composition solution at 55° C. to 65° C. for 20 minutes to 60 minutes.

Advantageous Effects

According to the present invention, a composition for a hydrogel sheet including a cellulose ether, a gelling agent, and a gelling promoter is provided so that a hydrogel sheet capable of maintaining the shape thereof without a support can be prepared.

A composition for a hydrogel sheet according to a first embodiment of the present invention can be used to prepare a hydrogel sheet that strongly adheres to the skin and has excellent stability and excellent moisturizing ability.

In addition, a composition for a hydrogel sheet according to a second embodiment of the present invention can be used to prepare a hydrogel sheet having excellent gel strength and high transparency because air bubbles present in a hydrogel sheet composition solution are easily removed through a brief deaerating process.

DESCRIPTION OF DRAWINGS

FIG. 1 is a flow chart of a method of preparing a hydrogel sheet according to an embodiment of the present invention.

FIG. 2 is a graph of comparing the hardness of each of hydrogels prepared according to Examples 1 to 8 and Comparative Examples 1 to 3.

FIG. 3 is a graph of comparing the moisture loss rate of each of hydrogel sheets prepared according to Examples 1 to 8 and Comparative Example 1.

FIG. 4 is a graph of comparing the adhesive force of each of hydrogels prepared according to Examples 1 to 8 and Comparative Examples 1 to 3.

FIG. 5 is an image of a hydrogel sheet prepared according to Example 9.

FIG. 6 is an image of a hydrogel sheet prepared according to Comparative Example 5.

BEST MODE

The present invention relates to a composition for a hydrogel sheet, a hydrogel sheet prepared therefrom, and a method of preparing the hydrogel sheet.

First, a composition for a hydrogel sheet according to the present invention will be described in accordance with the following two embodiments.

A composition for a hydrogel sheet according to a first embodiment of the present invention includes a cellulose ether, a gelling agent including carrageenan, and a gelling promoter.

The gelling agent is used to form a gel, adjust strength and syneresis, and improve usability, and a natural polymer may be used rather than a water-soluble synthetic polymer as the gelling agent to eliminate toxicity applied to skin. As in the first embodiment of the present invention, when carrageenan is included as the gelling agent, a hydrogel sheet which is capable of gelation at room temperature and maintaining the shape thereof without a support and has an excellent mechanical property such as excellent hardness or excellent strength may be prepared.

In the first embodiment of the present invention, the gelling agent may further include one or more selected from the group consisting of locust bean gum, mannose, and water chestnut flour. It is preferable that such gelling agents are used together with carrageenan as gelling agents because they may impart elasticity to a hydrogel.

A composition for a hydrogel sheet according to a second embodiment of the present invention includes a cellulose ether, a gelling agent, and a gelling promoter, wherein a viscosity of an aqueous 2 wt % cellulose ether solution measured under a condition of 20° C. using an Ubbelohde viscometer is 3 cps to 300 cps.

The cellulose ether refers to a cellulose derivative produced by etherifying the hydroxyl groups of cellulose. As in the second embodiment of the present invention, when a cellulose ether having a low viscosity is used, a large amount of air bubbles generated in a hydrogel sheet composition solution during a process of preparing the solution may naturally rise and be removed at a temperature of 55° C. to 65° C. Therefore, air bubbles may be easily removed through a brief deaerating process performed after the preparation of the hydrogel sheet composition solution, and in this way, a hydrogel sheet having excellent gel strength and a transparent appearance may be prepared.

In the second embodiment of the present invention, a commonly used natural polymeric gelling agent may be used as the gelling agent without limitation. For example, one or more selected from the group consisting of carrageenan, locust bean gum, mannose, and water chestnut flour may be used as the gelling agent. In particular, it is preferable that carrageenan alone or a combination of carrageenan and other gelling agent(s) is used as a gelling agent(s) so that a hydrogel capable of gelation at room temperature and having excellent gel strength may be prepared.

In the second embodiment of the present invention, a viscosity of an aqueous 5 wt % hydrogel sheet composition solution measured under conditions of 60° C. and 15 to 60 rpm using a Brookfield viscometer may be 500 cps to 5,000 cps. In this case, the viscosity of the aqueous composition solution is obtained by measuring a viscosity of a deaerated hydrogel sheet composition solution.

Hereinafter, common characteristics of the cellulose ether, the gelling agent, and the gelling promoter included in the composition for a hydrogel sheet according to the first or second embodiment will be described as follows.

The cellulose ether may include one or more selected from the group consisting of methyl cellulose, hydroxyethyl methyl cellulose, hydroxypropyl methyl cellulose, hydroxyethyl cellulose, hydroxypropyl cellulose, and carboxymethyl cellulose.

The gelling promoter may be used to improve the mechanical properties of the gelling agent. The gelling promoter serves to cross-link the gelling agent. The gelling promoter may be a Group 1 or 2 metal salt, and preferably includes one or more metal salts selected from the group consisting of magnesium chloride, potassium chloride, calcium chloride, and sodium chloride.

A molar ratio of a repeat unit of the gelling agent and a molar ratio of the gelling promoter, per a glucose unit of the cellulose ether, may be 0.01 to 12.00 and 0.01 to 2.00, respectively. When a molar ratio of a repeat unit of the gelling agent per a glucose unit of the cellulose ether is less than 0.01, the viscosity is very low, and it is difficult to form a gel, and thus characteristics of a gel may not be exhibited. On the other hand, when the molar ratio is greater than 12.00, the hardness of a gel is significantly high, and thus the gel may weakly adhere to the skin and have low usability. In addition, when a molar ratio of the gelling promoter per a glucose unit of the cellulose ether is less than 0.01, gel strength is too low, and thus the gel may be too soft and easily torn. On the other hand, when the molar ratio is greater than 2.00, the hardness of a gel is too high, and thus the gel may weakly adhere to the skin.

In addition, there is provided a hydrogel sheet prepared from the composition for a hydrogel sheet according to the first or second embodiment of the present invention.

The hydrogel sheet may have a porosity of 0.01% to 5%. When a porosity of the hydrogel sheet is less than 0.01%, economic feasibility with respect to a preparing process may be degraded. On the other hand, when the porosity is greater than 5%, the hydrogel sheet may exhibit low strength and have poor appearance due to low transparency. In this case, the porosity may be calculated based on an actual density and a theoretical calculated density of the hydrogel sheet, wherein the actual density is determined by measuring the weight and volume of the sheet.

The hydrogel sheet may be widely applied in the medical and pharmaceutical field and the cosmetic field, and is preferably used for a cosmetic mask pack or a wound dressing.

In addition, there is provided a method of preparing a hydrogel sheet from the composition for a hydrogel sheet according to any one of the first and second embodiments. The preparing method includes preparing a composition for a hydrogel sheet by mixing a cellulose ether, a gelling agent, and a gelling promoter; preparing a hydrogel sheet composition solution by inputting the composition for a hydrogel sheet into hot water and stirring the mixture; deaerating the hydrogel sheet composition solution by allowing air bubbles contained therein to rise; casting the deaerated hydrogel sheet composition solution in the form of a sheet; and gelating the casted sheet type hydrogel sheet composition solution.

Hereinafter, the method of preparing a hydrogel sheet according to an embodiment of the present invention will be described in detail for each step.

(1) Preparation of Composition for Hydrogel Sheet

In this step, a composition for a hydrogel sheet is prepared by mixing a cellulose ether, a gelling agent, and a gelling promoter.

In this case, ingredients of the composition for a hydrogel sheet and the mixing ratio thereof may be appropriately adjusted according to the first or second embodiment. For example, a gelling agent may include carrageenan according to the first embodiment of the present invention, or a viscosity of an aqueous 2 wt % cellulose ether solution measured under a condition of 20° C. using an Ubbelohde viscometer may be 3 cps to 300 cps according to the second embodiment of the present invention. Among conditions related to a type of the gelling agent and a viscosity of the cellulose ether, either one or both may be satisfied.

In addition, characteristics of each composition, such as a type of the cellulose ether, contents (molar ratios) of the gelling agent and the gelling promoter, a type of the gelling promoter, and the like, are as described above.

When a cellulose ether, a gelling agent, and a gelling promoter are mixed to prepare a composition for a hydrogel sheet as described above, and then the composition for a hydrogel sheet is input into hot water and stirred according to a step (2) to be described below, a process time required to perform a deaerating process according to a step (3) to be described below may be shortened compared to when a cellulose ether, a gelling agent, and a gelling promoter are input into hot water one at a time and stirred.

(2) Preparation of Hydrogel Sheet Composition Solution

In this step, a hydrogel sheet composition solution is prepared by inputting the composition for a hydrogel sheet into hot water and stirring the mixture to disperse and partially dissolve the composition.

A temperature of the hot water may be 70° C. to 100° C. When a temperature of the hot water is less than 70° C., a composition for a hydrogel sheet is not easily dispersed, nor is it partially dissolved, and thus it may be difficult to prepare a hydrogel sheet composition solution. Accordingly, the hydrogel sheet may have poor properties.

When the composition for a hydrogel sheet is dispersed and partially dissolved in hot water to prepare a hydrogel sheet composition solution, physical force is applied using a mechanical stirrer, which causes the generation of a large amount of air bubbles in the solution. When air bubbles are not removed from the solution, mechanical properties of the hydrogel sheet prepared from the composition, such as appearance, strength, and the like, are adversely affected.

Therefore, a step (3) of deaeration to be described below is performed to remove air bubbles.

(3) Deaeration

In this step, the hydrogel sheet composition solution is deaerated by allowing air bubbles contained therein to rise.

The deaeration may be performed by maintaining the hydrogel sheet composition solution at 55° C. to 65° C. for 20 minutes to 60 minutes. In particular, when a hydrogel sheet composition solution is prepared according to the step (2) by using a composition for a hydrogel sheet including a cellulose ether having a low viscosity of 3 cps to 300 cps, air bubbles generated in the solution may naturally rise and be removed at 55 to 65° C. In this case, when a temperature of the solution is maintained within the above range, air bubbles in the solution may be removed within 1 hour, and thus processing efficiency may be improved.

By easily removing air bubbles included in the hydrogel sheet composition solution through a brief deaerating process as described above, it may be possible to solve a problem caused by the air bubbles, for example, a problem in which air bubbles prevent the hydrogel from having a three-dimensional network structure, resulting in poor gel sheet properties such as low gel strength, or impart an opaque appearance to the hydrogel sheet, resulting in a low-quality hydrogel sheet.

When the composition for a hydrogel sheet includes a cellulose ether having a low viscosity according to the second embodiment, a viscosity of the deaerated hydrogel sheet composition solution (solid content of 5 wt %) measured under conditions of 60° C. and 15 to 60 rpm using a Brookfield viscometer may be 500 cps to 5,000 cps.

(4) Casting

In this step, the deaerated hydrogel sheet composition solution is casted in the form of a sheet.

Specifically, the deaerated hydrogel sheet composition solution may be casted to a thickness of 0.1 mm to 10.0 mm at room temperature to prepare a hydrogel sheet. When the thickness is less than 0.1 mm, a hydrogel sheet may be torn due to a low strength. On the other hand, when the thickness is greater than 10 mm, the sheet may weakly adhere to the skin and the delivery efficiency of an active ingredient may be low.

(5) Gelation

In this step, the casted sheet type hydrogel sheet composition solution is gelated.

The gelation may be performed according to a method commonly used in the related art. For example, when carrageenan alone or a combination of carrageenan and other gelling agent(s) is used as a gelling agent(s), the gelation may be performed by naturally maintaining the solution at room temperature.

Hereinafter, the present invention will be described in more detail with reference to embodiments of the present invention. However, the present invention is not limited by the following embodiments.

<Analysis of Hydrogel Sheet Properties According to Type of Gelling Agent>

Example 1

Hydroxypropyl methyl cellulose (HPMC) (HPMC 2910 commercially available from Lotte Fine Chemical Co., Ltd.), carrageenan (MSC Co., Ltd.), and potassium chloride (Sigma Aldrich) were mixed to prepare a composition for a hydrogel sheet. In this case, carrageenan and potassium chloride were mixed at a ratio of 0.3 mole (based on a repeat unit) and 0.07 mole, respectively, per 1 mole of a glucose unit of HPMC. That is, HPMC, carrageenan, and potassium chloride were mixed at a molar ratio of 1:0.3:0.07.

Subsequently, the composition for a hydrogel sheet was input into 85° C. hot water, and the mixture was stirred to prepare a hydrogel sheet composition solution. In this case, a total content of solids (the composition for a hydrogel sheet) in the hydrogel sheet composition solution was 5.08 wt %.

Subsequently, the hydrogel sheet composition solution was maintained at 60° C. for 60 minutes to perform a deaerating process in which air bubbles generated in the solution naturally rose and then were discharged to the outside.

Subsequently, the deaerated hydrogel sheet composition solution was casted to a thickness of 0.1 mm at room temperature and then gelated to prepare a hydrogel sheet.

Examples 2 to 8 and Comparative Examples 1 to 4

Hydrogel sheets were prepared in the same manner as in Example 1 except that a molar ratio of HPMC, a type and a molar ratio of a gelling agent, a type and a molar ratio of a gelling promoter, and a total solid content were adjusted as listed in Table 1 below.

TABLE 1

| | HPMC (molar ratio) | Gelling agent | | Gelling promoter | | Total solid content (wt %) |
| | | Type | Total content (molar ratio) | Type | Total content (molar ratio) | |
| --- | --- | --- | --- | --- | --- | --- |
| Example 1 | 1.0 | Carrageenan | 0.3 | KCl | 0.07 | 5.08 |
| Example 2 | 1.0 | Carrageenan | 0.3 | $MgCl_2$ | 0.06 | 5.08 |
| Example 3 | 1.0 | Carrageenan | 0.3 | $CaCl_2$ | 0.05 | 5.08 |
| Example 4 | 1.0 | Carrageenan | 0.3 | NaCl | 0.09 | 5.08 |
| Example 5 | 1.0 | Carrageenan | 0.3 | KCl | 0.07 | 5.78 |
| | | Locust bean gum (LBG) | 0.1 | | | |
| Example 6 | 1.0 | Carrageenan | 0.3 | KCl | 0.07 | 5.78 |
| | | Water chestnut flour | 0.1 | | | |
| Example 7 | 1.0 | Carrageenan | 0.3 | $MgCl_2$ | 0.06 | 5.78 |
| | | LBG | 0.1 | | | |
| Example 8 | 1.0 | Carrageenan | 0.3 | KCl | 0.07 | 6.28 |
| | | LBG | 0.1 | | | |
| | | Mannose | 0.2 | | | |

TABLE 1-continued

|  | HPMC (molar ratio) | Gelling agent | | Gelling promoter | | Total solid content (wt %) |
|---|---|---|---|---|---|---|
|  |  | Type | Total content (molar ratio) | Type | Total content (molar ratio) |  |
| Comparative Example 1 | 0.0 | Carrageenan LBG | 0.3 0.1 | MgCl$_2$ | 0.14 | 2.78 |
| Comparative Example 2 | 1.0 | Xanthan gum LBG | 0.3 0.1 | MgCl$_2$ | 0.06 | 4.71 |
| Comparative Example 3 | 1.0 | Gellan gum LBG | 0.3 0.1 | MgCl$_2$ | 0.06 | 7.08 |
| Comparative Example 4 | 1.0 | Guar gum LBG | 0.3 0.1 | MgCl$_2$ | 0.06 | 5.78 |

HPMC: Lotte Fine Chemical Co., Ltd./HPMC 2910 (hydroxypropyl methyl cellulose)
Carrageenan: MSC Co., Ltd./carrageenan
Locust bean gum: LBG Sicilia Ingredients/SEED GUM A-200
Water chestnut flour: Upvas/Singoda Flour
Mannose: Sigma Aldrich/D-(+)-Mannose
Xanthan gum: Danisco/Grindsted Xanthan 80
Gellan gum: CP Kelco/Kelcogel LT 100
Guar gum: Lotus gum & Chemicals/guar gum
KCl: Sigma Aldrich/potassium chloride
MgCl$_2$: Samchun Pure Chemical/magnesium chloride, anhydrous, 98.0%
CaCl$_2$: Samchun Pure Chemical/calcium chloride, anhydrous, 96.0%
NaCl: Samchun Pure Chemical/sodium chloride, 99%

In Table 1, the molar ratio refers to a molar ratio of a gelling agent or a gelling promoter per a glucose unit of HPMC, and a molar ratio of a repeat unit in the case of a gelling agent. In addition, the total solid content represents a weight ratio of solid with respect to the total weight of each of the hydrogel sheets according to Examples 1 to 8 and Comparative Examples 1 to 4 as percentage.

Evaluation Example 1: Measurement of Hardness of Gel

Each of the deaerated hydrogel sheet composition solutions according to Examples 1 to 8 and Comparative Examples 1 to 4 was input into a beaker and gelated, and the hardness of a gel was measured. In this case, the hardness was measured using a Brookfield CT3 texture analyzer under conditions of a cylindrical probe, a trigger load of 4.0 g, and a speed of 0.5 mm/s.

FIG. 2 is a graph of comparing the hardness of each of hydrogels prepared according to Examples 1 to 8 and Comparative Examples 1 to 3.

Referring to FIG. 2, it can be seen that hydrogels prepared according to Examples 1 to 8 in which carrageenan was included had higher hardnesses than hydrogels prepared according to Comparative Example 2 and Comparative Example 3 in which xanthan gum and gellan gum were included as a gelling agent, respectively. Also, in the case of Comparative Example 4 in which guar gum was included, a gel was insufficiently formed, and thus hardness measurement was not possible.

Evaluation Example 2: Measurement of Moisture Loss Rate

Each of the deaerated hydrogel sheet composition solutions according to Examples 1 to 8 and Comparative Example 1 was used to prepare a hydrogel fragment having a size of 3.0 cm (width)×3.0 cm (length) and a thickness of 0.1 cm. The hydrogel fragment was dried at room temperature, and weights thereof before and after being dried were measured using a balance (FX-3000i, A&D Company Limited, Japan). Then, a moisture loss rate was calculated by Equation 1 below.

Moisture loss rate (%)={(Weight of fragment before being dried−Weight of fragment after being dried)/Weight of fragment before being dried}× 100  [Equation 1]

FIG. 3 is a graph of the moisture loss rate according to Examples 1 to 8 and Comparative Example 1.

Referring to FIG. 3, it can be seen that the hydrogel sheets prepared according to Examples 1 to 8 in which HPMC was used had moisture loss rates similar to that of the hydrogel sheet prepared according to Comparative Example 1 in which HPMC was not used.

Evaluation Example 3: Measurement of Adhesive Force

Each of the hydrogels prepared according to Examples 1 to 8 and Comparative Examples 1 to 3 was used to measure adhesive force using a Brookfield CT3 texture analyzer under conditions of a cylindrical probe and a speed of 0.5 mm/s.

FIG. 4 is a graph of comparing the adhesive force of each of hydrogels prepared according to Examples 1 to 8 and Comparative Examples 1 to 3.

Referring to FIG. 4, it can be seen that the hydrogels prepared according to Examples 1 to 8 had adhesive forces higher than the hydrogels prepared according to Comparative Examples 1 to 3.

<Analysis of Hydrogel Sheet Properties According to Viscosity of Cellulose Ether>

Example 9

HPMC (HPMC 2910 commercially available from Lotte Fine Chemical Co., Ltd.), carrageenan (MSC Co., Ltd.), locust bean gum (LBG Sicilia Ingredients), and potassium chloride (Sigma Aldrich) were mixed to prepare a composition for a hydrogel sheet. In this case, carrageenan, locust bean gum, and potassium chloride were mixed at a ratio of 0.3 mole (based on a repeat unit), 0.1 mole (based on a repeat unit), and 0.07 mole, respectively, per 1 mole of a glucose unit of HPMC. That is, HPMC, a gelling agent (carrageenan+locust bean gum), and potassium chloride were mixed at a molar ratio of 1:0.4:0.07. Also, a viscosity of an aqueous 2 wt % HPMC solution measured at 20° C. using an Ubbelohde viscometer was 15 cps.

Subsequently, the composition for a hydrogel sheet was input into 85° C. hot water, and the mixture was stirred to prepare a hydrogel sheet composition solution. In this case, a total content of solids (the composition for a hydrogel sheet) in the hydrogel sheet composition solution was 5 wt %.

Subsequently, the hydrogel sheet composition solution was maintained at 60° C. for 60 minutes to perform a deaerating process in which air bubbles generated in the solution naturally rose and then were discharged to the outside. In this case, a viscosity of the deaerated hydrogel sheet composition solution (solid content of 5 wt %) measured under conditions of 60° C. and 60 rpm using a Brookfield viscometer was 1,677 cps.

Subsequently, the deaerated hydrogel sheet composition solution was casted to a thickness of 0.1 mm at room temperature and then was gelated to prepare a hydrogel sheet.

Examples 10 to 12 and Comparative Examples 5 and 6

Hydrogel sheets were prepared in the same manner as in Example 9 except that a viscosity of the aqueous 2 wt % HPMC solution and a viscosity of the deaerated hydrogel sheet composition solution were as listed in Table 2 below.

Evaluation Example 4

The degree of air bubbles remaining in the hydrogel sheet composition solution that have been maintained at 60° C. for 60 minutes according to Examples 9 to 12 and Comparative Examples 5 and 6 (i.e., the degree of deaeration) was observed with the naked eye.

In Table 2 below, "x" means a state in which almost all of air bubbles have risen, leaving a transparent solution in which a small number of air bubbles remain at an upper part thereof. Also, "Δ" means a state in which a lower part of the solution is transparent, but an upper part of the solution is covered with a thick layer of air bubbles, and "o" means a state in which air bubbles remain throughout the solution.

Evaluation Example 5

Each of the hydrogel sheets prepared according to Examples 9 to 12 and Comparative Examples 5 and 6 was cut into a size of 7 cm (width)×7 cm (length) to prepare a specimen, and the specimen was used to measure the strength of the gel sheet, the result of which is shown in Table 2 below. In this case, measurement conditions are as follows.

Device: Brookfield CT3 texture analyzer
Probe: TA41 (cylindrical probe)
Fixture base table: Ta-BT-KTI
Test type: compression
Target type: distance
Target value: 30 mm
Trigger load: 2 g
Test speed: 0.5 mm/s

TABLE 2

| | Viscosity of HPMC (cps) | Viscosity of composition for hydrogel sheet (cps) | Degree of deaeration | Strength of gel sheet (g) |
|---|---|---|---|---|
| Example 9 | 15 | 1,677 | x | 101.5 |
| Example 10 | 150 | 3,354 | x | 100.8 |
| Example 11 | 200 | 3,818 | x | 93.4 |
| Example 12 | 300 | 4,184 | x | 89.3 |
| Comparative Example 5 | 400 | 5,562 | Δ | 74.3 |
| Comparative Example 6 | 500 | 6,202 | o | 74.8 |

Referring to Table 2, it can be confirmed that Examples 9 to 12, in which a viscosity of an aqueous 2 wt % HPMC solution was 3 cps to 300 cps, exhibited a viscosity of a deaerated hydrogel sheet composition solution (solid content of 5 wt %) within a range of 500 cps to 5,000 cps, and a state in which almost all of air bubbles had risen after 60 minutes of the deaerating process, leaving a transparent hydrogel sheet composition solution containing only a small number of air bubbles remaining at an upper part thereof. On the other hand, the hydrogel sheet composition solutions according to Comparative Examples 5 and 6, which were prepared from compositions for a hydrogel sheet including HPMC outside the above viscosity range, exhibited a state in which an upper part of the solution was covered with a thick layer of air bubbles, or a state in which air bubbles remained throughout the solution even after 60 minutes of the deaerating process.

FIGS. 5 and 6 illustrate images of hydrogel sheets prepared according to Example 9 and Comparative Example 5, respectively. Referring to FIGS. 5 and 6, it can be confirmed that no air bubble was observed in the hydrogel sheet prepared according to Example 9, whereas a large amount of air bubbles was observed in the hydrogel sheet prepared according to Comparative Example 5.

In addition, it can be confirmed that the hydrogel sheets prepared according to Examples 9 to 12 exhibited strengths higher than those of Comparative Examples 5 and 6.

The examples disclosed in the present invention are intended to illustrate, not limit, the technical spirit of the present invention, and the scope of the present invention should be interpreted by the appended claims and to encompass all equivalents falling within the scope of present invention.

The invention claimed is:

1. A method of preparing a hydrogel sheet, the method comprising:
   preparing a composition for a hydrogel sheet by mixing a cellulose ether, a gelling agent, and a gelling promoter;
   preparing a hydrogel sheet composition solution by inputting the composition for a hydrogel sheet into hot water and performing stirring;
   deaerating the hydrogel sheet composition solution by allowing air bubbles contained therein to rise;
   casting the deaerated hydrogel sheet composition solution in the form of a sheet; and
   gelating the casted sheet type hydrogel sheet composition solution,
   wherein an aqueous 2 wt % solution of the cellulose ether has a viscosity of 15 cps to 300 cps, as measured under a condition of 20° C. using an Ubbelohde viscometer.

2. The method of claim 1, wherein a temperature of the hot water is 70° C. to 100° C.

3. The method of claim 1, wherein the deaeration is performed by maintaining the hydrogel sheet composition solution at 55° C. to 65° C. for 20 minutes to 60 minutes.

* * * * *